(12) United States Patent
Pedrotti

(10) Patent No.: US 8,406,616 B2
(45) Date of Patent: Mar. 26, 2013

(54) TABLET AND DEVICE FOR THE EVAPORATION OF VOLATILE SUBSTANCES

(75) Inventor: Andrea Pedrotti, Trento (IT)

(73) Assignee: Zobele Holding SpA (IT)

( * ) Notice: Subject to any disclaimer, the term of this patent is extended or adjusted under 35 U.S.C. 154(b) by 382 days.

(21) Appl. No.: 12/600,880

(22) PCT Filed: Jun. 27, 2008

(86) PCT No.: PCT/EP2008/058273
§ 371 (c)(1),
(2), (4) Date: Feb. 8, 2010

(87) PCT Pub. No.: WO2009/003944
PCT Pub. Date: Jan. 8, 2009

(65) Prior Publication Data
US 2010/0166816 A1    Jul. 1, 2010

Related U.S. Application Data

(60) Provisional application No. 60/947,050, filed on Jun. 29, 2007.

(51) Int. Cl.
*F24F 6/00*    (2006.01)

(52) U.S. Cl. ................................ 392/390; 392/391

(58) Field of Classification Search ............. 392/390, 392/391
See application file for complete search history.

(56) References Cited

U.S. PATENT DOCUMENTS 5,201,025 A * 4/1993 Landesberg ............... 392/392

FOREIGN PATENT DOCUMENTS

| EP | 0498278 | 8/1992 |
|---|---|---|
| EP | 0538527 | 4/1993 |
| GB | 2166653 | 5/1986 |
| GB | 2166653 A * | 5/1986 |
| WO | 97/45008 | 12/1997 |

OTHER PUBLICATIONS

International Search Report; PCT/EP2008/058273; Dec. 9, 2008.

\* cited by examiner

*Primary Examiner* — Ali Soroush
(74) *Attorney, Agent, or Firm* — Cantor Colburn LLP

(57) ABSTRACT

The present invention refers to a tablet (1) for retaining a volatile substance in a liquid or solid state, such as a perfume and/or an insecticide. The tablet comprises at least a first and a second layers (2,4) of volatile substance retaining material, said first and second layers being spaced apart from each other at a selected distance, and wherein it further comprises a layer of impermeable material (3) joined to said layers and located in between said first and second layers.

8 Claims, 4 Drawing Sheets

TABLET AND DEVICE FOR THE EVAPORATION OF VOLATILE SUBSTANCES

OBJECT OF THE INVENTION

The present invention refers to a tablet for retaining a volatile substance in a liquid or solid state, such as a perfume and/or an insecticide.

BACKGROUND ART

Tablets and evaporation devices using these type of tablets are described for instance in the patent publications WO 97/45008 and EP-0.498.278. Typically, these tablets are a flat body and are arranged parallel to the heating means of an electric evaporation device.

It is known that this type of tablets provide a "a first step of high evaporation rate" effect the first time there are used, so that a great amount of volatile substance is evaporated and dispersed to the ambient in a short time, the first time that the tablet is used in an electric evaporation device. Subsequently, after said first step of high evaporation rate, the amount of volatile substance diffused to the ambient is reduced significantly and progressively until its complete evaporation.

DESCRIPTION OF THE INVENTION

A first aspect of the invention refers to a tablet for the evaporation of volatile substances, which comprises a first and a second layers of volatile substance retaining material, for example a porous material. In the present invention porous material refers to a any type of porous material, including porous plastics. The two layers may have the same or different properties in respect for example: porosity, material, thickness, content of volatile substance etc.

The tablet is configured in such a manner that the volatile substance in one of the layers can evaporate faster than the volatile substance in the other layer.

The tablet of the invention can be used in the following modes:

Two different formulations and/or active substances are provided for a multi-target product (flies/mosquitoes).

Two different active substances with different temperature release.

Same active substance but with different release (evaporation surface & temperature), to get for instance a first step of high evaporation rate, and a long active release.

DESCRIPTION OF THE DRAWINGS

To complement the description being made and with the object of aiding towards a better understanding of the characteristics of the invention, in accordance with a preferred example of embodiment thereof, a set of drawings is attached as an integral part of said description, wherein the following has been represented, with an illustrative, non-limiting character.

PREFERRED EMBODIMENT OF THE INVENTION

In a preferred embodiment, said first and second layers (2,4) are spaced apart from each other at a selected distance. Preferably, the two porous layers are spaced from each other by means of a layer of impermeable material (3), which is joined to said layers and located in between said first and second layers. Alternatively, the layer of impermeable material (3) consist of a surface of one of said layers having impermeable properties.

Figure 1:
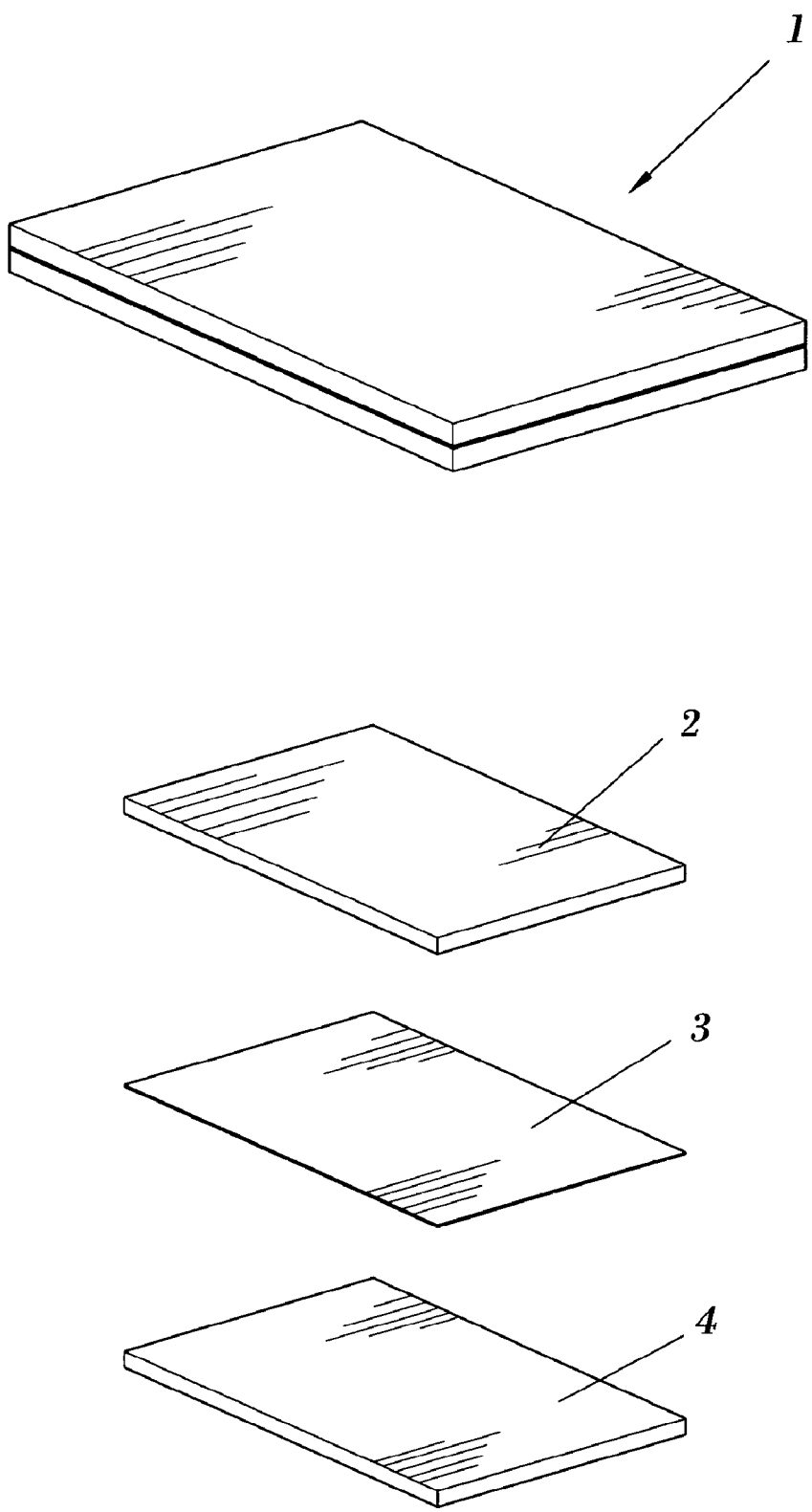
FIG. 1.—shows two perspective views of the tablet, the one at the left in an exploded view of the tablet.
Figure 2:
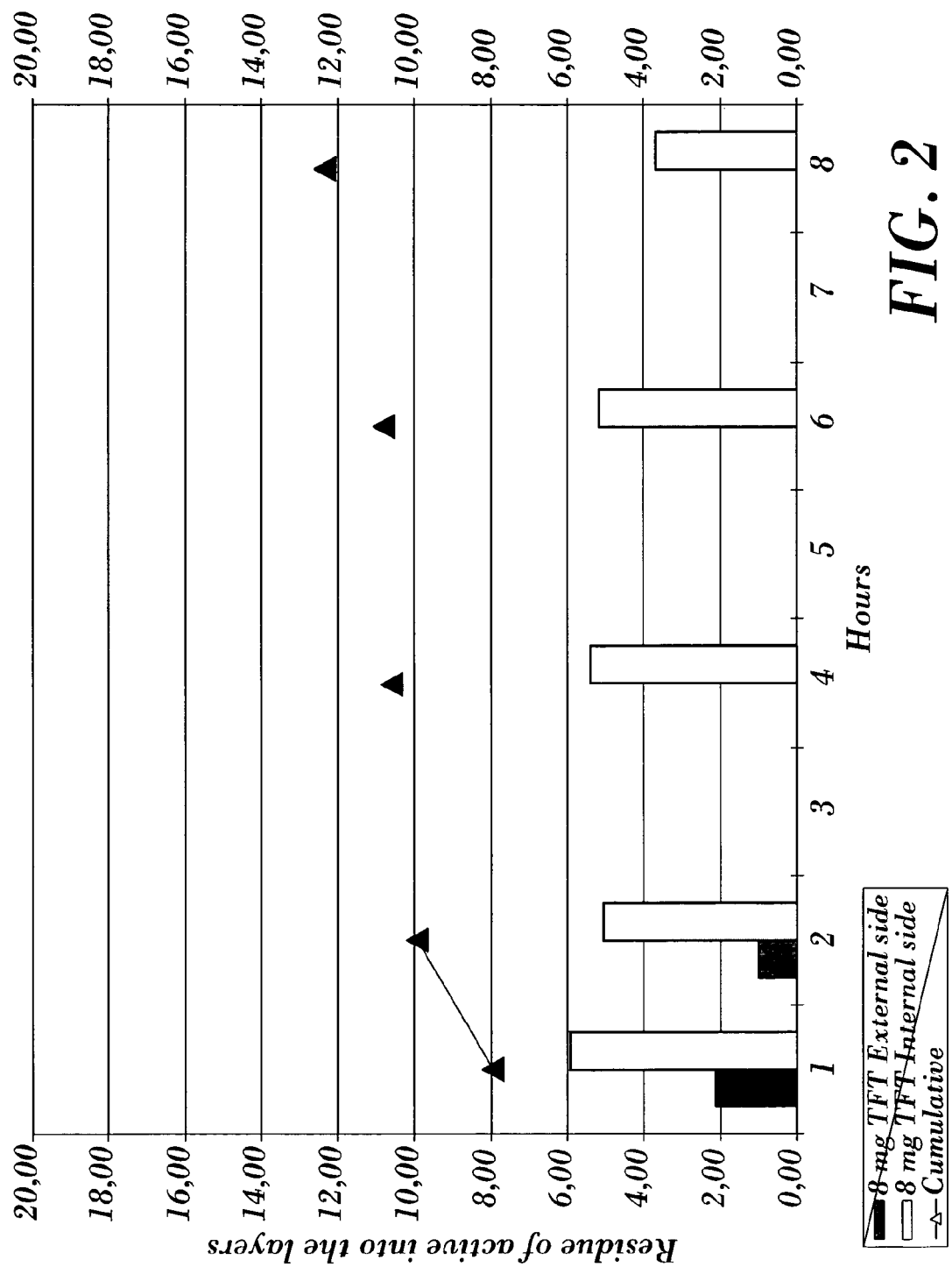
FIG. 2.—shows a bar diagram indicative the weight loss of the two volatile substances of a dual layer tablet, when both tables contain the same amount and type of volatile substance (8 mg TFT+8 mg TFT). It can be seen the high evaporation rate of a first substance in the external layer (darker bar), and the slow and constant evaporation rate of the second substance in the internal layer of the tablet (lighter bar).
Figure 3:
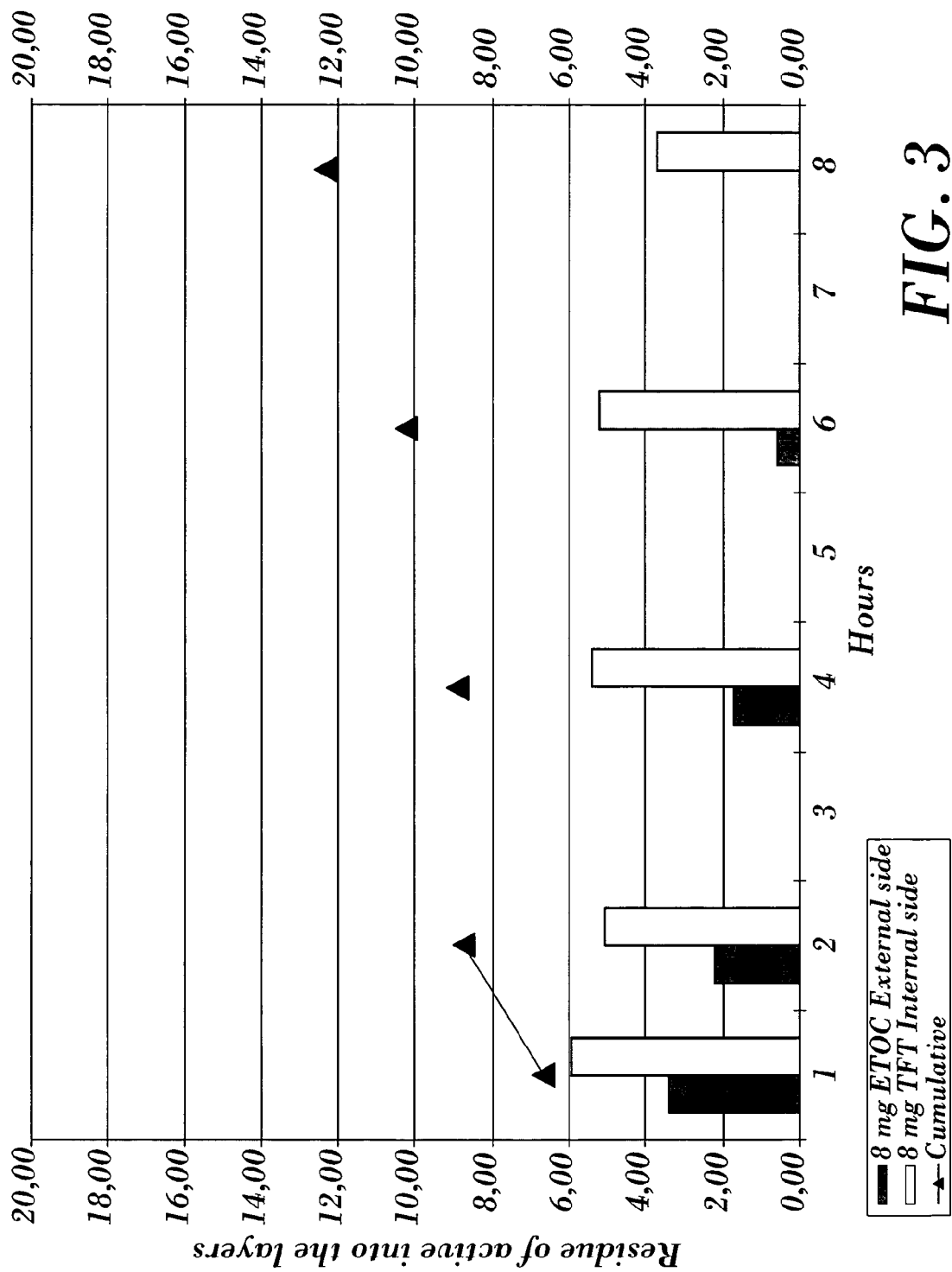
FIG. 3.—shows a bar diagram indicative the weight loss of the two volatile substances of a dual layer tablet, when the two tables contain different type of volatile substances (8 mg ETOC+8 mg TFT). It can be seen the high evaporation rate of a first substance (darker bar), and the slow and constant evaporation rate of the second substance (lighter bar).

The tablet of the present invention provides a double effect, because the tablet is formed by two layers of a substance retaining material, so that each layer can be affected by different evaporation conditions when the tablet is used in an evaporation device as shown in FIG. 1.

In FIG. 1 it can be observed that the tablet of the invention is formed by a top layer (2), a bottom layer (4) and an impermeable layer (3) located in between said layers. The tablet is conventionally placed above or close to a heater element of an evaporation device. The bottom layer (4) is closer to the heater than the top layer.

Additionally, it can be seem how the upper face and the side faces of the top layer (2) are open to the surrounding air, whereas only the sides faces of the bottom layer are open. The lower face of the bottom layer is closed by the heater surface, and its upper face is closed by the impermeable layer. Consequently, only the side faces of the bottom layer allow the evaporation of the volatile substance.

Alternatively, the tablet can be used in a non-electric evaporation device wherein the bottom layer lays on a surface the casing of the device so that the surface of said layer is closed.

The reduced evaporation surface of one layer (just the perimeter) permits using a large range of actives ingredients (also the ones with high vapour pressure that evaporate too fast in the standard mat).

In an exemplary embodiment of the invention, both layers of porous material are impregnated with the same amount of an insecticide, so that the insecticide retained by the top layer would be evaporated massively thereby obtaining a "a first step of high evaporation rate" effect generating an "insecticide action" killing the insects within the range of the device. The insecticide in the bottom layer would evaporate slower because only the side faces of this layer are in contact with the air, so that a "repellent action" is obtained because only a limited amount of insecticide is diffused to the air which maintains other insects away from the proximity of the device.

Alternatively, the top and bottom layers are impregnated with different perfumes so that the tablet could be used in both positions, that is with the top or bottom layer located closer to the heating means. The user could therefore select which perfume would be used for an effect of high evaporation rate and which perfume would be used for a slower evaporation action.

Figure 4:
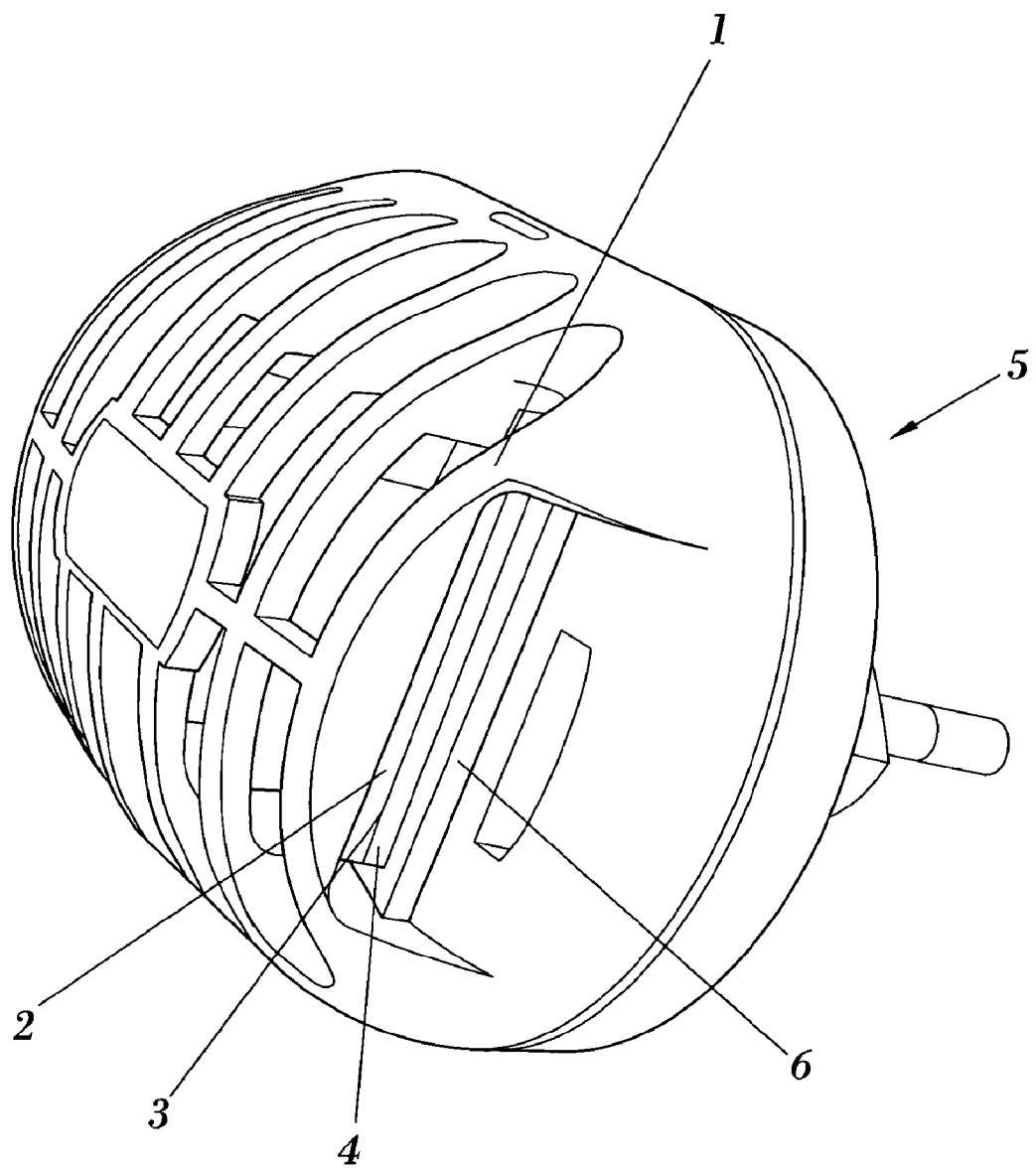
FIG. 4.—is a perspective view of an electric evaporation device having a tablet according to the invention.

FIG. 4 shows an device for the evaporation of volatile substances (5) comprising a heating element (6) and a tablet (1) arranged in the device in such a manner that one of said layers, in this case the layer (4) is closer to the heating element (6) than the other layer (2).

The invention claimed is:

1. A device for the evaporation of volatile substances comprising a heating element and a tablet, said tablet comprising:
 a top layer and a bottom layer, each layer having a volatile substance retaining material, the device further comprising:
 a layer of impermeable material joined to said top and bottom layers and located in between said top and bottom layers, wherein the tablet is arranged in the device in such a manner that the bottom layer is closer to the heating element than the to layer.

2. The device according to claim 1 wherein the top and bottom layers are made of a porous material.

3. The device according to claim 1 wherein the top and bottom layers are impregnated with a liquid volatile substance, said substance comprising an insecticide and/or a perfume.

4. The device according to claim 1 wherein the top and bottom layers are, made, of a porous material having different absorption capacity.

5. The device according to claim 1 wherein the top and bottom layers are impregnated with a volatile substance having different composition.

6. The device according to claim 1 wherein the top and bottom layers, and the impermeable layer have the same shape in a plan view.

7. The device according to claim 1 wherein the tablet is placed above the heating element.

8. The device according to claim 1 wherein the top layer is impregnated with the same volatile substance as the bottom layer.

* * * * *